US010279084B2

(12) United States Patent
Goepfrich et al.

(10) Patent No.: US 10,279,084 B2
(45) Date of Patent: May 7, 2019

(54) MEDICAL BALLOON DEVICES AND METHODS

(71) Applicant: W. L. Gore & Associates, Inc., Newark, DE (US)

(72) Inventors: James L. Goepfrich, Flagstaff, AZ (US); Joshua C. Haarer, Flagstaff, AZ (US); Brandon C. Hedberg, Flagstaff, AZ (US); Benjamin M. Trapp, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 14/132,767

(22) Filed: Dec. 18, 2013

(65) Prior Publication Data

US 2014/0172066 A1 Jun. 19, 2014

Related U.S. Application Data

(60) Provisional application No. 61/783,345, filed on Mar. 14, 2013, provisional application No. 61/739,650, filed on Dec. 19, 2012.

(51) Int. Cl.
*A61M 29/00* (2006.01)
*A61L 29/06* (2006.01)
(Continued)

(52) U.S. Cl.
CPC .............. *A61L 29/06* (2013.01); *A61F 2/958* (2013.01); *A61M 25/10* (2013.01);
(Continued)

(58) Field of Classification Search
CPC ... A61F 2/958; A61M 25/10; A61M 25/1029; A61M 2025/1084; A61M 2025/1086;
(Continued)

(56) References Cited

U.S. PATENT DOCUMENTS

| 3,953,566 A | 4/1976 | Gore |
| 4,187,390 A * | 2/1980 | Gore .................... B01D 71/36 |
| | | 128/205.12 |

(Continued)

FOREIGN PATENT DOCUMENTS

| EP | 0 293 090 | 11/1988 |
| EP | 0 313 263 A2 | 4/1989 |

(Continued)

OTHER PUBLICATIONS

International Search Report and Written Opinion for PCT/US2011/061165 dated Oct. 1, 2012, corresponding to U.S. Appl. No. 13/298,060.
(Continued)

*Primary Examiner* — Elizabeth Houston
*Assistant Examiner* — Kankindi Rwego

(57) ABSTRACT

A balloon or balloon cover comprising a composite material having a least one expanded fluoropolymer material and an elastomer is provided. The expanded fluoropolymer material can contain serpentine fibrils. In exemplary embodiments, the fluoropolymer is polytetrafluoroethylene. The composite material may be axially, helically, and/or circumferentially wrapped to form a balloon or balloon cover. The balloon or balloon cover exhibits a sharp increase in stiffness at a predetermined diameter. The balloon or balloon cover can be designed to have a stop point in either a radial or axial direction.

34 Claims, 15 Drawing Sheets

(51) Int. Cl.
  *A61F 2/958* (2013.01)
  *A61M 25/10* (2013.01)
(52) U.S. Cl.
  CPC . *A61M 25/1029* (2013.01); *A61M 2025/1084* (2013.01); *A61M 2025/1086* (2013.01)
(58) Field of Classification Search
  CPC ........ A61M 25/104; A61M 2025/1081; B29K 2027/18
  USPC ........ 606/194; 264/127, 288.4, 288.8, 289.3, 264/289.6, 290.2, 290.5, 290.7
  See application file for complete search history.

(56) References Cited

U.S. PATENT DOCUMENTS

| | | | |
|---|---|---|---|
| 4,332,035 | A | 6/1982 | Mano |
| 4,877,661 | A | 10/1989 | House et al. |
| 4,955,899 | A | 9/1990 | Della Corna et al. |
| 5,026,513 | A | 6/1991 | House et al. |
| 5,071,609 | A | 12/1991 | Tu et al. |
| 5,476,589 | A * | 12/1995 | Bacino ............... B01D 39/1692 210/500.36 |
| 5,534,007 | A | 7/1996 | St. Germain et al. |
| 5,549,663 | A | 8/1996 | Cottone |
| 5,708,044 | A | 1/1998 | Branca |
| 5,718,973 | A | 2/1998 | Lewis et al. |
| 5,752,934 | A * | 5/1998 | Campbell ............ A61L 29/085 604/96.01 |
| 5,759,192 | A | 6/1998 | Saunders |
| 5,769,884 | A | 6/1998 | Solovay |
| 5,772,884 | A | 6/1998 | Tanaka et al. |
| 5,824,043 | A | 10/1998 | Cottone |
| 5,843,158 | A | 12/1998 | Lenker et al. |
| 5,843,161 | A | 12/1998 | Solovay |
| 5,853,419 | A | 12/1998 | Imran |
| 5,925,061 | A | 7/1999 | Ogi et al. |
| 5,935,162 | A | 8/1999 | Dang |
| 6,010,529 | A | 1/2000 | Herweck et al. |
| 6,013,854 | A | 1/2000 | Moriuchi |
| 6,042,588 | A | 3/2000 | Munsinger et al. |
| 6,042,606 | A | 3/2000 | Frantzen |
| 6,174,329 | B1 | 1/2001 | Callol et al. |
| 6,190,406 | B1 | 2/2001 | Duerig et al. |
| 6,217,609 | B1 | 4/2001 | Haverkost |
| 6,245,012 | B1 | 6/2001 | Kleshinski |
| 6,261,320 | B1 | 7/2001 | Tam et al. |
| 6,336,937 | B1 | 1/2002 | Vonesh et al. |
| 6,436,132 | B1 | 8/2002 | Patel et al. |
| 6,488,701 | B1 | 12/2002 | Nolting et al. |
| 6,541,589 | B1 | 4/2003 | Baillie |
| 6,620,190 | B1 | 9/2003 | Colone |
| 6,626,939 | B1 | 9/2003 | Burnside et al. |
| 6,673,107 | B1 | 1/2004 | Brandt et al. |
| 6,730,120 | B2 | 5/2004 | Berg et al. |
| 6,755,856 | B2 | 6/2004 | Fierens et al. |
| 6,758,858 | B2 | 7/2004 | McCrea et al. |
| 7,049,380 | B1 | 5/2006 | Chang et al. |
| 7,083,642 | B2 | 8/2006 | Sirhan et al. |
| 7,105,018 | B1 | 9/2006 | Yip et al. |
| 7,306,729 | B2 | 12/2007 | Bacino et al. |
| 7,419,678 | B2 | 9/2008 | Falotico |
| 7,531,611 | B2 | 5/2009 | Sabol et al. |
| 7,789,908 | B2 | 9/2010 | Sowinski et al. |
| 7,811,314 | B2 | 10/2010 | Fierens et al. |
| 7,815,763 | B2 | 10/2010 | Fierens et al. |
| 7,927,364 | B2 | 4/2011 | Fierens et al. |
| 7,927,365 | B2 | 4/2011 | Fierens et al. |
| 7,935,141 | B2 | 5/2011 | Randall et al. |
| 7,967,829 | B2 | 6/2011 | Gunderson et al. |
| 8,585,753 | B2 | 11/2013 | Scanlon |
| 2002/0076542 | A1 | 6/2002 | Kramer et al. |
| 2002/0198588 | A1 | 12/2002 | Armstrong et al. |
| 2003/0060871 | A1 | 3/2003 | Hill et al. |
| 2003/0180488 | A1 | 9/2003 | Lim et al. |
| 2004/0024442 | A1 * | 2/2004 | Sowinski ............... A61L 27/16 623/1.13 |
| 2004/0024448 | A1 | 2/2004 | Chang et al. |
| 2004/0133266 | A1 | 7/2004 | Clerc et al. |
| 2004/0170782 | A1 | 9/2004 | Wang et al. |
| 2004/0260277 | A1 * | 12/2004 | Maguire ............ A61B 18/1492 606/28 |
| 2005/0080476 | A1 | 4/2005 | Gunderson et al. |
| 2005/0137680 | A1 | 6/2005 | Ortiz et al. |
| 2005/0283224 | A1 | 12/2005 | King |
| 2006/0009835 | A1 | 1/2006 | Osborne et al. |
| 2006/0036311 | A1 | 2/2006 | Nakayama et al. |
| 2006/0106337 | A1 | 5/2006 | Blankenship |
| 2006/0135985 | A1 | 6/2006 | Cox et al. |
| 2006/0259133 | A1 | 11/2006 | Sowinski et al. |
| 2006/0271091 | A1 | 11/2006 | Campbell et al. |
| 2006/0276883 | A1 | 12/2006 | Greenberg et al. |
| 2007/0012624 | A1 | 1/2007 | Bacino et al. |
| 2007/0060999 | A1 | 3/2007 | Randall et al. |
| 2007/0129786 | A1 | 6/2007 | Beach et al. |
| 2007/0208421 | A1 | 9/2007 | Quigley |
| 2007/0213800 | A1 | 9/2007 | Fierens et al. |
| 2007/0250146 | A1 | 10/2007 | Cully et al. |
| 2007/0250153 | A1 | 10/2007 | Cully et al. |
| 2007/0254012 | A1 | 11/2007 | Ludwig et al. |
| 2008/0051876 | A1 | 2/2008 | Ta et al. |
| 2008/0097301 | A1 * | 4/2008 | Alpini ............... A61M 25/1029 604/103.07 |
| 2008/0097582 | A1 | 4/2008 | Shanley et al. |
| 2008/0119943 | A1 | 5/2008 | Armstrong et al. |
| 2008/0319531 | A1 | 12/2008 | Doran et al. |
| 2009/0005854 | A1 | 1/2009 | Huang et al. |
| 2009/0030499 | A1 | 1/2009 | Bebb et al. |
| 2009/0043373 | A1 | 2/2009 | Arnault de la Menardiere et al. |
| 2009/0182413 | A1 | 7/2009 | Burkart et al. |
| 2010/0094394 | A1 | 4/2010 | Beach et al. |
| 2010/0094405 | A1 | 4/2010 | Cottone |
| 2010/0106240 | A1 | 4/2010 | Duggal et al. |
| 2010/0159171 | A1 | 6/2010 | Clough |
| 2010/0256738 | A1 | 10/2010 | Berglund |
| 2012/0323211 | A1 * | 12/2012 | Ogle ....................... A61K 47/32 604/500 |
| 2013/0131780 | A1 | 5/2013 | Armstrong et al. |
| 2013/0183515 | A1 * | 7/2013 | White ................... B29C 55/005 428/297.4 |
| 2013/0184807 | A1 | 7/2013 | Kovach et al. |
| 2013/0253466 | A1 | 9/2013 | Campbell et al. |
| 2013/0297003 | A1 | 11/2013 | Pinchuk |
| 2014/0135897 | A1 | 5/2014 | Cully et al. |
| 2014/0180402 | A1 | 6/2014 | Bruchman et al. |
| 2015/0313871 | A1 | 11/2015 | Li et al. |
| 2016/0015422 | A1 | 1/2016 | De Cicco et al. |

FOREIGN PATENT DOCUMENTS

| | | |
|---|---|---|
| EP | 0 815 806 | 1/1997 |
| EP | 0 893 108 | 1/1999 |
| JP | H02645 A | 1/1990 |
| JP | H09241412 | 9/1997 |
| JP | H11290448 | 10/1999 |
| JP | 2008/506459 A | 3/2008 |
| JP | 2010-535075 A | 11/2010 |
| JP | 2010/05315075 A | 11/2010 |
| RU | 2124986 C1 | 1/1994 |
| WO | 95/05555 | 2/1995 |
| WO | 1996040348 A1 | 12/1996 |
| WO | 97/010871 | 3/1997 |
| WO | 00/41649 | 7/2000 |
| WO | WO-00/47271 A1 | 8/2000 |
| WO | WO-01/64278 A1 | 9/2001 |
| WO | 01/74272 | 10/2001 |
| WO | 02/060506 | 8/2002 |
| WO | 2004/000375 | 12/2003 |
| WO | WO-2006/019626 A2 | 2/2006 |
| WO | 2008/021002 | 2/2008 |
| WO | 2008/028964 | 3/2008 |
| WO | 2008/036870 | 3/2008 |
| WO | 2008/049045 | 4/2008 |

(56) References Cited

FOREIGN PATENT DOCUMENTS

| WO | 2009/017827 A1 | 2/2009 |
|---|---|---|
| WO | WO-2009/17827 A1 | 2/2009 |
| WO | 2009/100210 | 8/2009 |
| WO | WO-2010/006783 A1 | 1/2010 |
| WO | 2010/030766 | 3/2010 |
| WO | 2010/132707 | 11/2010 |
| WO | 2012099979 A1 | 7/2012 |
| WO | 2013/109337 | 7/2013 |

OTHER PUBLICATIONS

International Search Report and Written Opinion for PCT/US2012/064910 dated Feb. 1, 2013, corresponding to U.S. Appl. No. 13/675,764, 8 pages.

International Search Report and Written Opinion for PCT/US2012/064908 dated Feb. 4, 2013, corresponding to U.S. Appl. No. 13/675,730, 11 pages.

International Search Report and Written Opinion for PCT/US2012/066518, dated Feb. 4, 2013, corresponding to U.S. Appl. No. 13/351,052, 12 pages.

Partial International Search Report for PCT/US2012/065066, dated Jul. 1, 2013, corresponding to U.S. Appl. No. 13/675,959, 3 pages.

Nakayama, Yasuhide. Microporous Stent Achieves Brain Aneurysm Occlusion Without Disturbing Branching Flow. NeuroNews Nov. 2012; 8:1-2.

Nishi S, Nakayama Y, Ishibashi-Ueda H, Okamoto Y, Yoshida M. Development of microporous self-expanding stent grafts for treating cerebral aneurysms: designing micropores to control intimal hyperplasia. J Artif Organs 2011; 14:348-356.

International Search Report for PCT/US2012/065066, dated Nov. 11, 2013, corresponding to U.S. Appl. No. 13/675,959, 10 pages.

Google Image Search Results, "S-Shaped", accessed Nov. 1, 2013.

International Search Report for PCT/US2013/076405 dated May 6, 2014,corresponding to U.S. Appl. No. 14/132,767, 8 pages.

International Search Report for PCT/US2014/013496 dated Dec. 2, 2014,corresponding to U.S. Appl. No. 13/755,481, 4 pages.

International Search Report and Written Opinion for Application No. PCT/US2016/028671 dated Jul. 28, 2016.

\* cited by examiner

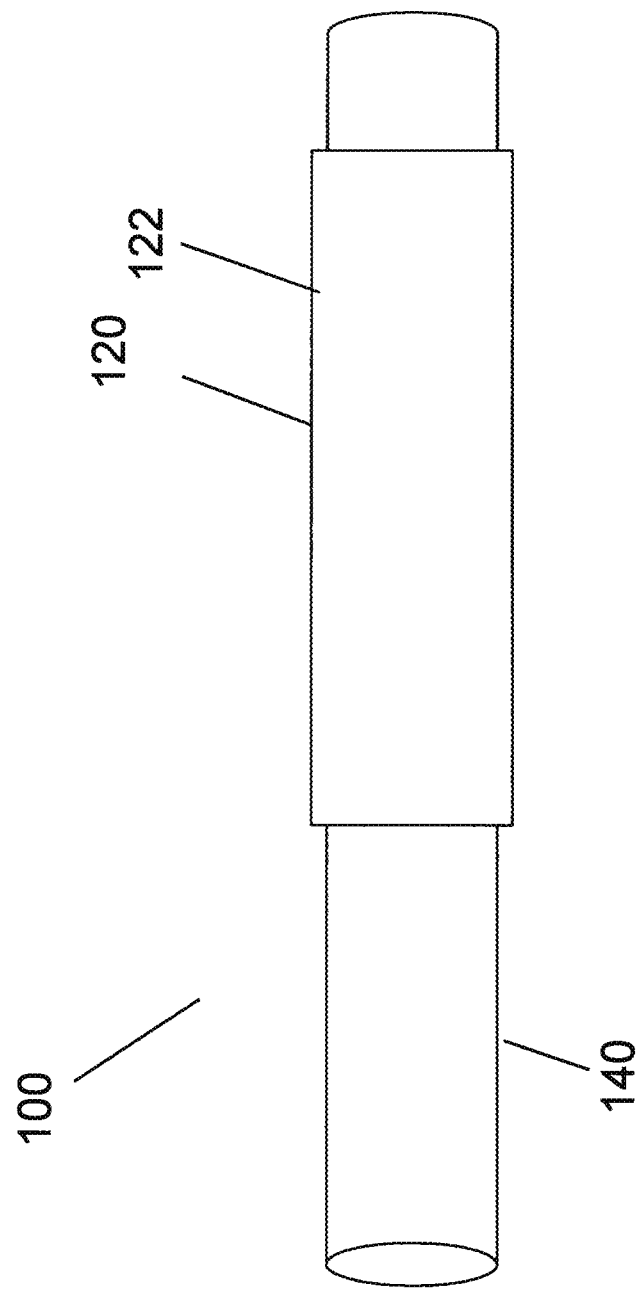

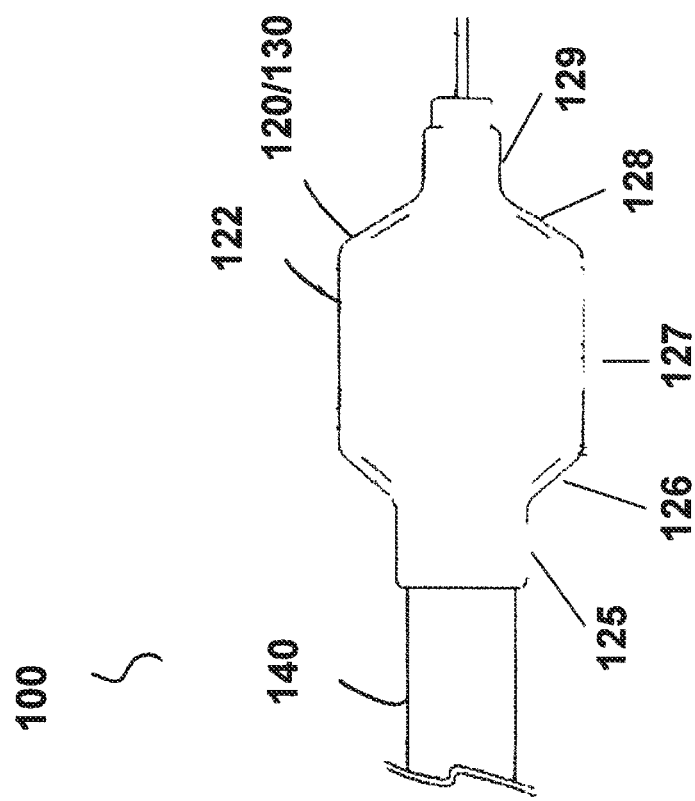

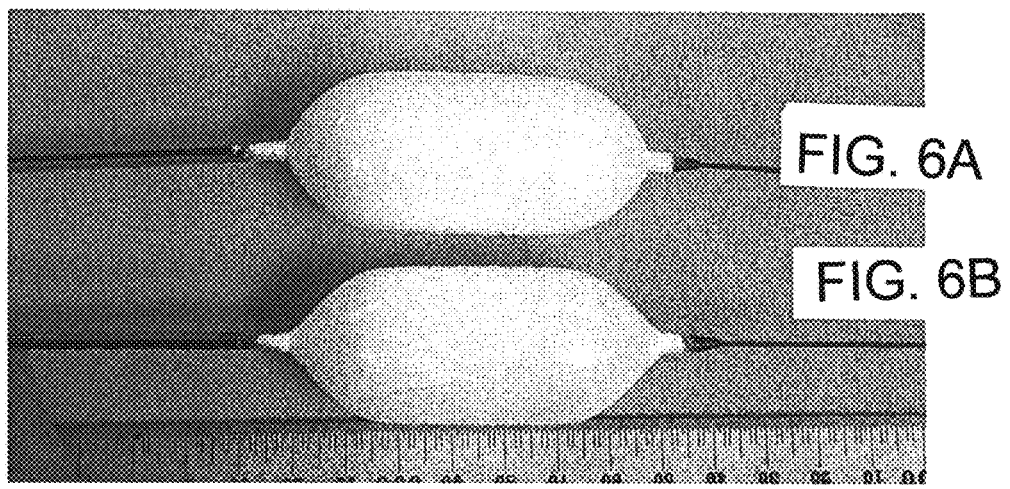

MEDICAL BALLOON DEVICES AND METHODS

FIELD

The present disclosure relates generally to balloon devices that are radially distensible up to a stop point in addition to being longitudinally distensible. The present disclosure relates generally to balloon devices that include (1) an expanded polytetrafluoroethylene (ePTFE) membrane material containing serpentine fibrils and (2) an elastomer.

DEFINITIONS

As used herein, the term "serpentine fibrils" means multiple fibrils that curve or turn one way then another.

As used herein, the term "controlled retraction" refers to causing articles to shorten in length in at least one direction by the application of heat, by wetting with a solvent, or by any other suitable means or combinations thereof in such a way as to inhibit folding, pleating, or wrinkling of the subsequent article visible to the naked eye.

The term "imbibed or imbibing" as used herein is meant to describe any means for at least partially filling at least a portion of the pores of a porous material such as ePTFE or the like.

The term "elastic" as used herein refers to the property of a material to be elongated upon the application of a force and that at least partially returns to its approximate original dimensions upon the release of the force due to the retraction force of the material.

The term "elongation" or "elongated" as used herein is meant to denote the increase in length in a particular direction (e.g., axial length) or an increase in perimeter or circumference of a particular cross-section in response to the application of a force. The term "distention" or "distended" as used herein is used interchangeable with "elongation" or "elongated".

The term "stiffness" as used herein refers the change in resistance to further elongation or distension.

The term "delivery diameter" as used herein refers to the diameter or cross-sectional width of a tubular form that is substantially equal to or slightly larger than the diameter or cross-sectional width of the tubular form during delivery through the vasculature, pre-inflation.

The term "nominal diameter" as used herein refers to the diameter or cross-sectional width of a balloon or balloon cover when the balloon has been circumferentially distended up to a stop point beyond which the force required to distend is markedly increased. Typically, the nominal diameter is the labeled diameter as indicated on the instructions for the end user, e.g., a clinician.

BACKGROUND

Wrapped film balloons are typically made by wrapping a film tube at a large second diameter (approximate to the desired nominal diameter) and then drawing the film tube down to reduce it to a first diameter and then compressing to store length to allow for subsequent fibril reorientation upon inflation. While this process is very involved, all of the subsequent steps are in order to reduce its diameter to a point making it suitable for mounting on a catheter.

An alternate method of making a balloon would be to wrap a layered membrane construct directly at a smaller, first diameter (a diameter approximate to the delivered diameter). In order to construct a wrapped film balloon at a smaller $1^{st}$ diameter, the film of which the balloon is constructed would need to distend 300-700% or more at least along the direction oriented around the circumference. A film that could distend 300-700% or more would facilitate construction of a balloon or balloon cover wrapped directly at a smaller ($1^{st}$) diameter. That is, it could be circumferentially wrapped in a tube at a small first diameter so that the distensible direction of the film is oriented along the circumference of the balloon. Upon inflation, the circumference would grow, distending the film from a $1^{st}$ diameter to a $2^{nd}$ diameter.

Previous film wrapped balloon or balloon covers capable of being constructed at a first diameter and distensible up to a nominal diameter (300% to 700% or more) were highly anisotropic films where the weak direction was oriented circumferentially to allow for distension. Balloons of this construction have some limitations which make them less than optimal.

For example, because the strong direction of the anisotropic film provides strength to the balloon wall in the longitudinal direction, the balloon wall is limited in its ability to distend in the longitudinal direction to account for inflation. As the balloon is inflated, the longitudinal distance from seal to seal increases because of the inflated profile. As the underlying balloons forms its inflated shape, the cover needs to grow in the longitudinal direction to account for this path change. This path change is greater for larger diameter balloons and for balloons with steeper cone angles.

Compounding this issue seems to lie in the tendency for a highly anisotropic film to foreshorten in the longitudinal direction to allow for radial distension. So while the balloon wall tends to lengthen to account for the path length change, the balloon wall tends to foreshorten to allow for radial distension because of the anisotropic film. The degree of foreshortening increases for increasing balloon diameters. This inability to distend longitudinally and the tendency to foreshorten impacts the ability to inflate fully and causes unwanted stress on the material some of which is transferred to the catheter causing buckling and in the case of a cover, to the underlying balloon causing cone rounding.

Some remedial measures can be made in attempts to minimize the undesired effects of these tendencies such as manually storing length by longitudinally compressing the material. However, this is an extra processing step, and adds bulk to the cover. Also, this extra length that can be stored is relatively mobile and can migrate/bunch undesirably during processes such as sheath insertion.

Another limitation of the above described constructs relate to the weak direction being oriented circumferentially. Such balloon or balloon covers have a very limited ability to influence the final burst properties of the balloon as the material will continue to distend until it splits with very little force.

Therefore, a circumferentially wrapped balloon or balloon cover, wrapped at a small ($1^{st}$) diameter, that can reduce the amount of foreshortening, can allow for an appropriate amount of longitudinal lengthening during high amounts of a radial distention (to allow for full inflation) can be beneficial, and can provide increased wall strength along the circumferential direction to increase burst.

SUMMARY OF THE DISCLOSURE

It is an object of the present disclosure to utilize fluoropolymer membrane that exhibit high elongation while substantially retaining the strength properties of the fluoropolymer membrane. Such fluoropolymer membranes characteristically possess serpentine fibrils, as such the membranes store length on a fibril level.

The present disclosure describes balloon devices that utilize an expanded polymer such as a fluoropolymer material that is optionally imbibed with an elastomer, which upon inflation, is circumferentially distensible up to a stop point beyond which the force required to distend is markedly increased. This stored length due to the serpentine shape of the fibrils can account for at least a portion of the radial distention. In addition, the described balloon devices can be also appropriately longitudinally distensible (or longitudinally weak) thereby giving or increasing in longitudinal length under the longitudinal stress that may otherwise occur during radial expansion. In various embodiments, construction of the described balloon or balloon devices comprises circumferentially wrapping the described elastomer-imbibed expanded polymeric material at a delivery diameter. Upon deflation, the balloon or balloon devices will at least partially re-compact to its deflated conformation, which can be, in various embodiments, approximately the delivery diameter.

The present disclosure describes balloon devices that include either (1) a medical balloon, e.g., a balloon having a proximal seal and shoulder region, a distal seal and shoulder region, and an intermediate working region there between or (2) a balloon cover disposed about an underlying balloon. The balloon or balloon cover can include a composite material that includes at least one expanded polymer membrane, such as an expanded fluoropolymer, and an elastomer. The composite material has a stop point beyond which little or no further expansion occurs without an increasing amount of force. That is, the composite material can be radially expanded or elongated to a point at which further distension is inhibited by an increase in stiffness. The expanded polymeric membrane includes serpentine fibrils. The fluoropolymer can be polytetrafluoroethylene. The fluoropolymer membrane can include a microstructure of substantially only serpentine fibrils. Furthermore, expanded polymeric membrane can include a plurality of serpentine fibrils. The serpentine fibrils have a width of about 1.0 micron or less.

The present disclosure describes balloon devices that include either (1) a medical balloon, e.g., a balloon having a proximal seal and shoulder region, a distal seal and shoulder region, and an intermediate working region there between or (2) a balloon cover disposed about an underlying balloon, wherein the stiffness of the balloon device wall can vary along its length and/or circumference. Furthermore, the stiffness can be patterned to counter-balance the varying regions or sections of stiffness along the length of a balloon expandable device. This type of patterning can facilitate a more uniform deployment of the balloon expandable device. Alternatively, the stiffness can be patterned otherwise affect the nature of inflation of a standalone balloon; for example, varying the stiffness to force the distal end and/or proximal end of a balloon to inflate first or the middle section of the balloon to inflate first). This type of patterning can be used to control blood flow during deployment or angioplasty. A balloon that inflated in a controllable manner could arrest blood flow on a proximal end and/or distal end and lead to better delivery of a drug or could prevent emboli from immediately being released down stream allowing for aspiration prior to full deployment. In various embodiments, the stiffness can be varied by increasing or decreasing the number of layers along a section or in an area. The balloon or balloon cover can include a composite material that includes at least one expanded polymer membrane, such as an expanded fluoropolymer, and an elastomer. The composite material has a stop point beyond which little or no further expansion occurs without an increase in force. That is, the composite material can be radially expanded or elongated to a point at which further distension is inhibited by an increase in stiffness. The expanded polymeric membrane includes serpentine fibrils. The expanded polymer can be a fluoropolymer, such as polytetrafluoroethylene. The polymer membrane can include a microstructure of substantially only serpentine fibrils. Furthermore, expanded polymeric membrane can include a plurality of serpentine fibrils. The serpentine fibrils have a width of about 1.0 micron or less.

The present disclosure describes balloon devices that include either a medical balloon or balloon cover comprising a shape wherein varying the stop points of the composite material along the length of the balloon outlines the shape of the inflated balloon. In various embodiments, the shape can comprise a proximal waist and a proximal tapered region, a distal seal and distal tapered region, and an intermediate working region between the two tapered regions. In various embodiments, the composite material can be circumferentially wrapped or wrapped at substantially constant, opposing angles. The composite material can include at least one expanded polymer membrane, such as an expanded fluoropolymer, and an elastomer. The composite material has a stop point beyond which little or no further expansion occurs without an increase in force. That is, the composite material can be radially expanded or elongated to a point at which further distension is inhibited by an increase in stiffness. The expanded polymeric membrane includes serpentine fibrils. The fluoropolymer can be polytetrafluoroethylene. The fluoropolymer membrane can include a microstructure of substantially only serpentine fibrils. Furthermore, expanded polymeric membrane can include a plurality of serpentine fibrils. The serpentine fibrils have a width of about 1.0 micron or less.

The present disclosure describes a method of manufacturing a balloon device that includes (1) forming a tubular form comprising a composite material at approximately a delivery diameter and (2) placing the tubular form over a medical balloon to serve as a balloon cover. The composite material can be wrapped circumferentially or at a high angle to construct the tubular form. No steps are needed to reduce the diameter of the tubular form once constructed. The composite material includes at least one expanded fluoropolymer membrane and an elastomer. In at least one exemplary embodiment, the expanded fluoropolymer membrane can include a microstructure of substantially only serpentine fibrils. The fluoropolymer membrane can include a plurality of serpentine fibrils. The serpentine fibrils have a width of about 1.0 micron or less.

It is a feature of the disclosure that the reduction in infolding of the balloon or balloon cover allows for less material bulk and a smaller diameter (e.g., a smaller profile).

It is yet another feature of the present disclosure that the balloon or balloon cover can have elastic properties longitudinally, radially, or both longitudinally and radially.

The foregoing and other objects, features, and advantages of the disclosure will appear more fully hereinafter from a consideration of the detailed description that follows. It is to be expressly understood, however, that the drawings are for illustrative purposes and are not to be construed as defining the limits of the disclosure.

BRIEF DESCRIPTION OF THE FIGURES

The advantages of this disclosure will be apparent upon consideration of the following detailed disclosure of the disclosure, especially in conjunction with the accompanying drawings wherein:

FIG. 3A is a schematic illustration of balloon device in accordance with the present disclosure in a deflated conformation;

FIG. 5B is a schematic illustration of a balloon device in accordance with the present disclosure in an inflated conformation;

FIG. 6A is an image of a balloon device in accordance with the present disclosure circumferentially wrapped at a first diameter in an inflated conformation;

FIG. 6B is an image of a balloon device having a balloon cover constructed of a highly anisotropic fluoropolymer film circumferentially wrapped at a first diameter in an inflated conformation;

DETAILED DESCRIPTION OF THE DISCLOSURE

Figure 1:
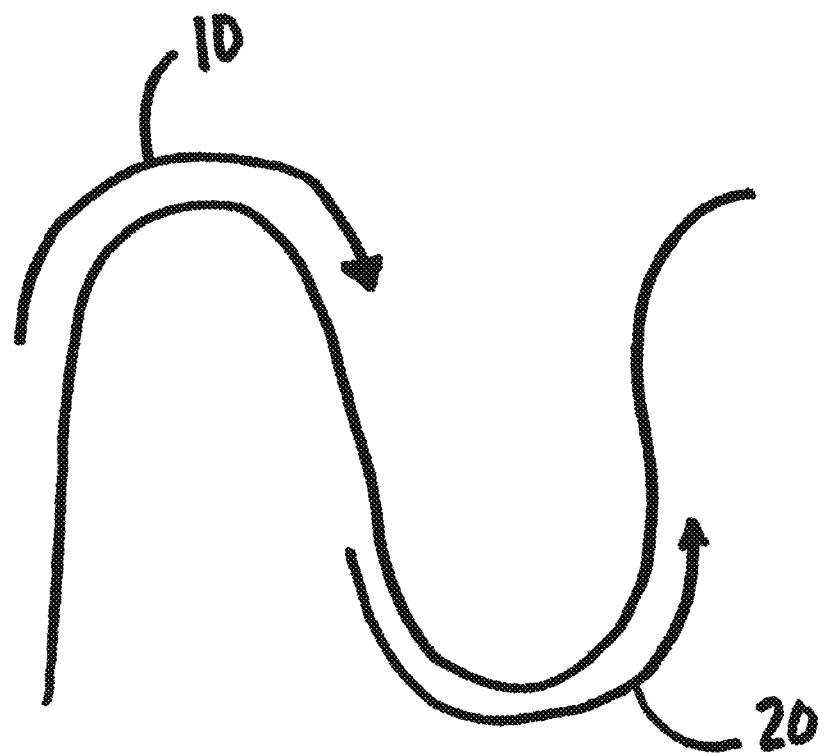
FIG. 1 is a schematic illustration of an exemplary, idealized serpentine fibril.

Unless defined otherwise, all technical and scientific terms used herein have the same meaning as commonly understood by one of ordinary skill in the art to which the disclosure belongs. In the drawings, the thickness of the lines, layers, and regions may be exaggerated for clarity. Like numbers found throughout the figures denote like elements.

The present disclosure is directed to a balloon device comprising an elastomeric balloon or balloon cover which is radially distensible up to a stop point in addition to being longitudinally distensible. A high amount of radial distensibility (about 150% to about 1000%) facilitates construction of a balloon or balloon cover at a delivery diameter (or width) which is smaller than the diameter of the device at the stop point. Constructing at a smaller diameter requires less material and thereby eliminates bulk, reducing the delivery and withdrawal profile of the device. In addition, constructing at a smaller diameter can eliminate any manufacturing steps required to reduce the profile through folding, necking, or otherwise working a component constructed at a nominal diameter.

In regard to longitudinal distension, some amount can be beneficial because generally tubular forms tend to foreshorten as they increase in diameter. In addition, as the balloon inflates, the seal-to-seal length along the surface of the balloon (i.e., profile length) is increased. If longitudinally distensible, the balloon cover can elongate to accommodate for any tension that occurs upon inflation. Accordingly, a described balloon cover can be less tensioned in the longitudinal direction and thus affording a longer and more cylindrical shape along the working region of the balloon device (e.g., less shoulder rounding) and less likely to rupture or split.

The present disclosure is directed to a balloon device comprising a composite material that has (1) an expanded polytetrafluoroethylene (ePTFE) material containing serpentine fibrils or other expanded polymer containing serpentine fibrils and optionally (2) an elastomer. The elastomer may be positioned on the ePTFE membrane and may also, or alternatively, be located in at least a portion of the pores of the ePTFE membrane. The elastomer may be present in all or substantially all of the pores of the ePTFE membrane. The term "substantially all of the pores" as used herein is meant to denote that the elastomer is present in at least a portion of all or nearly all of the pores of the ePTFE membrane. In one or more exemplary embodiments, the balloon comprises a fluoropolymer membrane.

The balloon or balloon cover of the disclosure may be employed in any body conduit or vessel, including arteries and veins. Balloons enable the dilation of a vessel, delivery of a therapeutic agent to a surrounding tissue, or the deployment of a medical device. The balloon cover can be optionally used to cover the outside of the balloon, e.g., to assist with re-compaction.

Figure 3B:
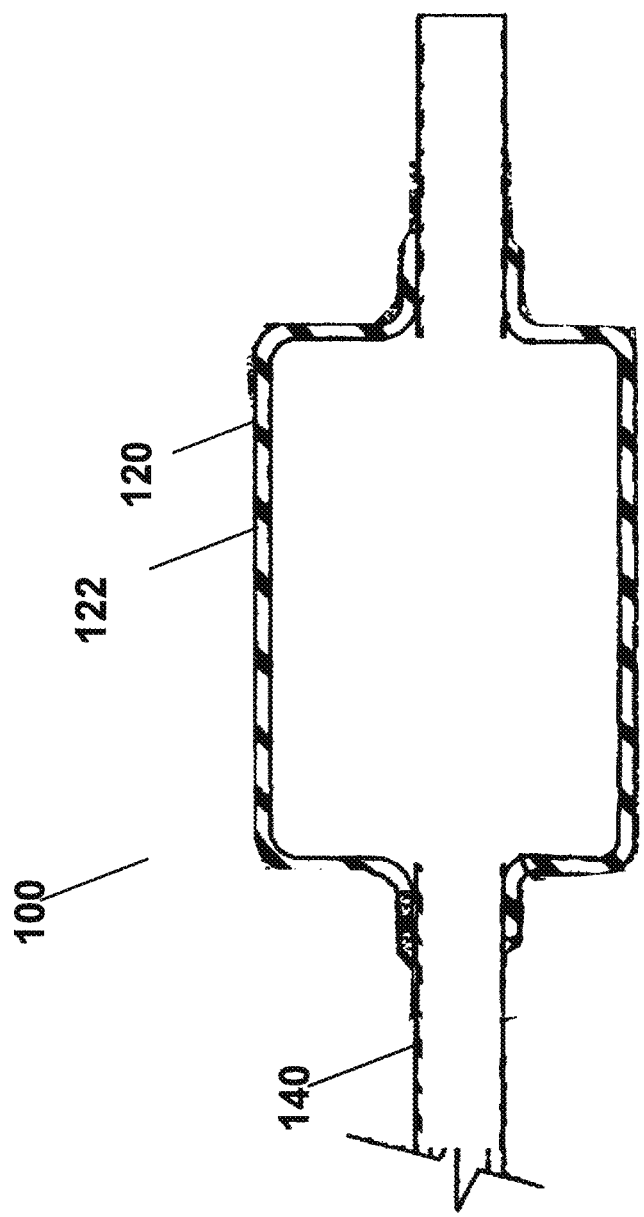
FIG. 3B is a schematic illustration of balloon device in accordance with the present disclosure in an inflated conformation.
Figure 4A:
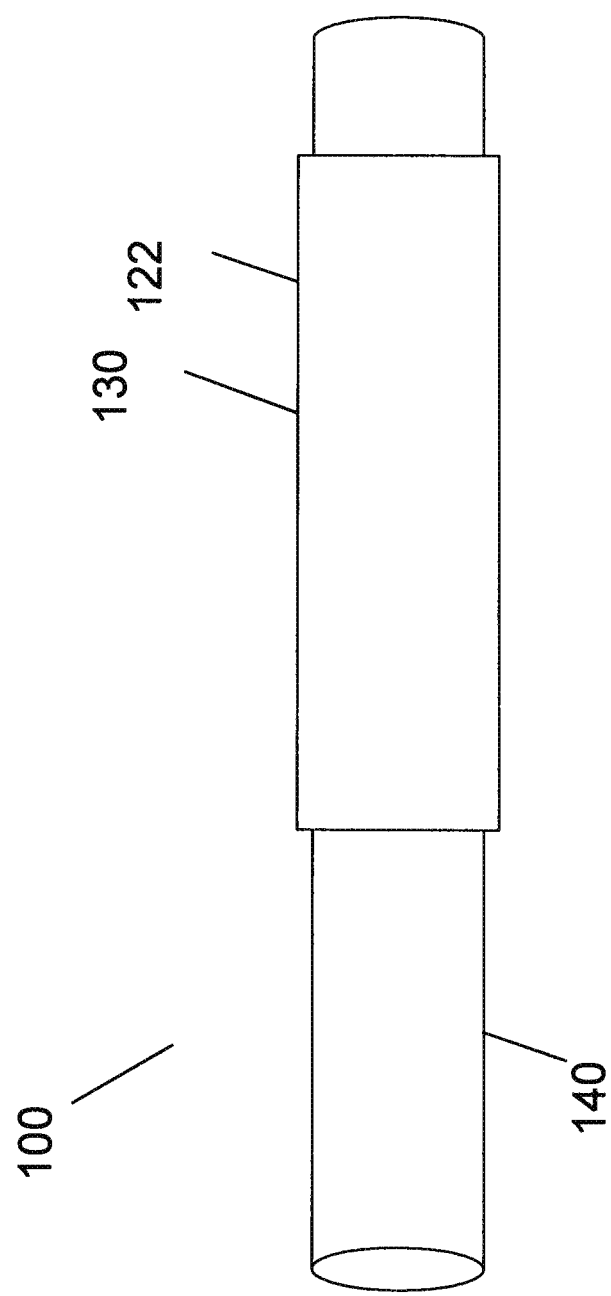
FIG. 4A is a schematic illustration of balloon and balloon cover in accordance with the present disclosure in a deflated conformation.
Figure 4B:
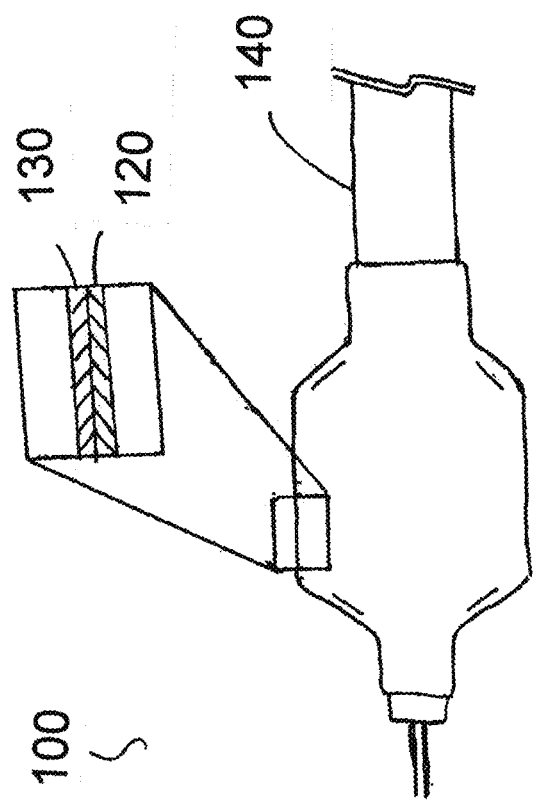
FIG. 4B is a schematic illustration of balloon and a balloon cover in accordance with the present disclosure in an inflated conformation.

With reference to FIGS. 3A and 3B, a balloon device 100 can comprise a balloon 120 mounted on a catheter 140 and comprise a deflated conformation and an inflated conformation. The balloon wall 122 can comprise the described composite material. The balloon wall 122 can comprise serpentine fibrils wherein the fibrils can be straightened along the circumference of the balloon wall upon inflation, thereby increasing the circumference of the balloon 120. The composite material can form the entire thickness of the balloon wall or only a portion thereof. Alternatively or in addition thereto, the composite material can form the entire length of balloon 120 or only a section thereof. Balloon 120 constructed of the described composite material will perform much like a compliant balloon. However, unlike a compliant balloon, balloon 120 will have an upper expansion limit or stop point. Thus, the internal pressure of balloon 120 can be higher than compliant-type balloons, and the material bulk can be less than non-compliant type balloons With reference to FIGS. 4A and 4B, a balloon device 100 can comprise a balloon 120 and a balloon cover 130 and be attached to a catheter 140 at or near a proximal and distal end, and have a deflated conformation and an inflated conformation. The balloon cover 130 can comprise the described composite material. The composite material can form the entire thickness of balloon cover 130 or only a portion thereof.

Figure 4C:
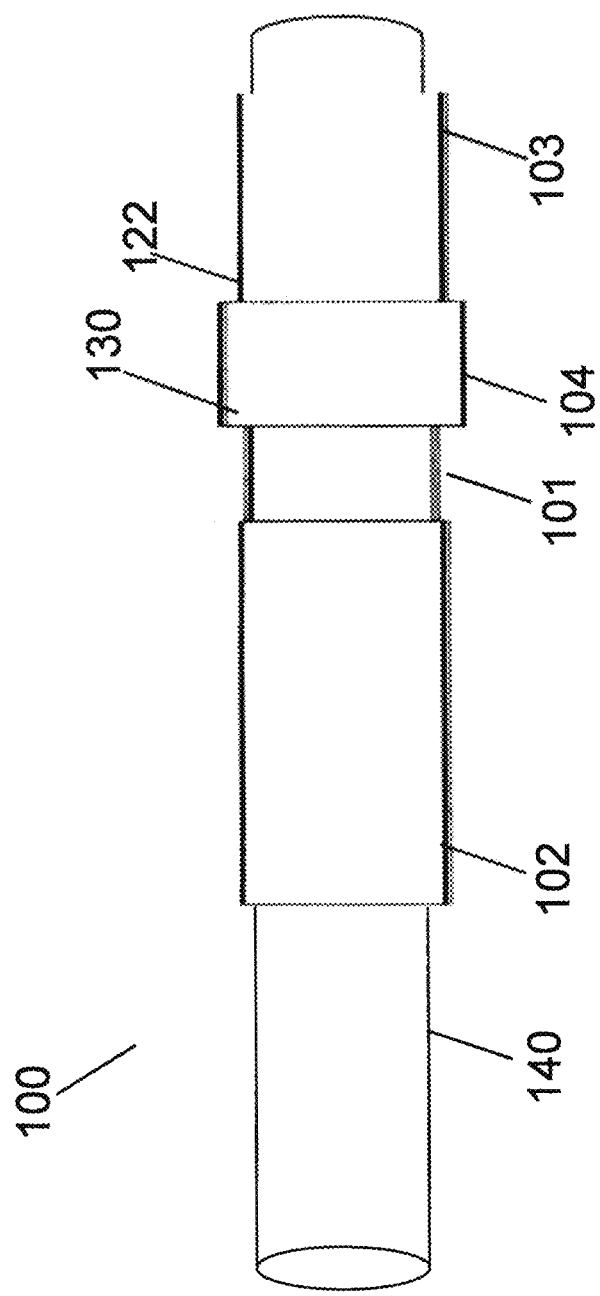
FIG. 4C is a schematic illustration of balloon and balloon cover comprising varied stiffness in accordance with the present disclosure in a deflated conformation.
Figure 4D:
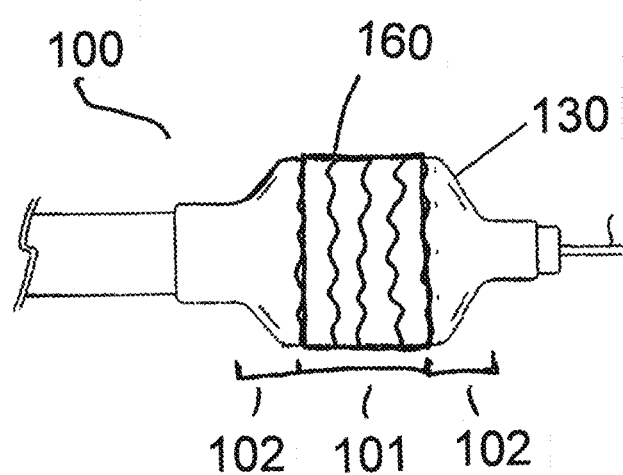
FIG. 4D is a schematic illustration of a balloon and a balloon cover having varied stiffness in accordance with the present disclosure with a stent device mounted on a section of the balloon device, in an inflated configuration.
Figure 4E:
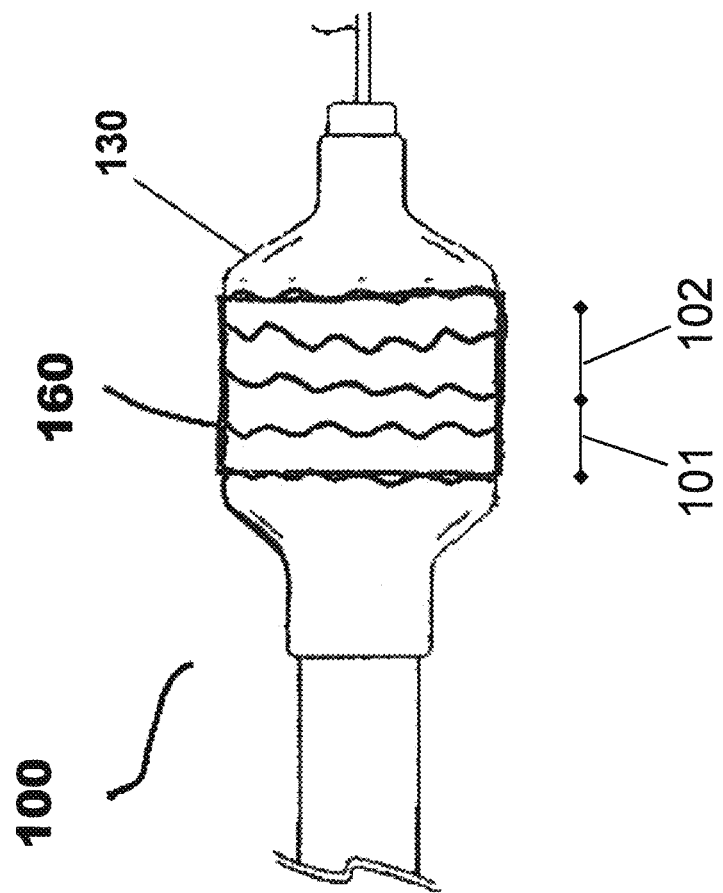
FIG. 4E is a schematic illustration of a balloon device in accordance with the present disclosure with a stent device mounted on a section of the balloon device, in an inflated configuration.

In various embodiments, the composite material can vary in thickness along its length, as is effectively illustrated in FIG. 4C with sections 101 to 104. For example, by increasing the number of wrapped layers in a given section of the length of balloon device 100, the more force is required to radially distend, and conversely, by decreasing the number of wrapped layers in a given section of the length of balloon device 100, the less force is required to radially distend. Such a construct can be useful to achieve more uniform or even inflation by accounting for, in the construction of the balloon or balloon cover, the stiffness caused by a medical device mounted about balloon device 100 during deployment. For example, with reference to FIG. 4C, a balloon device 100 comprises a balloon expandable stent 160 located at section 101. Along this section 101 of balloon device 100 more force will be required to distend that section 101 versus the sections 102 not covered by stent 160. By increasing the number of layers section(s) 102 not covered by stent 160, the forces can be counter-balanced, resulting in a device that inflates in a more uniform or desired manner. Similarly, with reference to FIG. 4D, if stent 160 or other device (e.g., a prosthetic heart valve) that is loaded on balloon device 100 varies in stiffness along the length of the device. For example, section 101 has more stiffness than section 102, the number of layers on the corresponding section of the balloon 100 can be tailored in order counterbalance those differences in stiffness.

In various embodiments, the underlying balloon 120 can comprise any type of medical balloon. Balloon 120 can be constructed of a compliant to non-compliant material. Balloon 120 can be a balloon made in accordance with the present disclosure. Balloons may be fabricated from a variety of commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenelyne Ether (PPE), Modified Polyphenelyne Ether (Mod PPE), Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluoroethylene (ECTFE), Ethylene, Ethylene Tetrafluoroethylene (ETFE), Polychlortrifluoroethylene (PCTFE), Polytetrafluoroethylene (PTFE), Polyvinylidene Fluoride (PVDF), Perfluoroalkoxy (PFA), or combinations, copolymers, or derivatives thereof. Other commonly known medical grade materials include elastomeric organosilicon polymers, polyether block amide or thermoplastic copolyether (e.g., PEBAX®).

As previously described, a balloon cover that comprises stored length in the fibrils which are oriented circumferentially can accommodate for the longitudinal tension that result from the increased dimensions of an inflated balloon. By comparison, a balloon cover material that does not allow for sufficient elongation upon expansion can result in more pronounced shoulder-rounding and/or rupture. For example, as shown in FIG. 6A, a balloon cover constructed with the weak direction oriented along the circumference (and a high strength oriented along the length) and covering a nylon balloon as set forth in Example 3 exhibits shoulder-rounding and a shortened working length, whereas, as shown in FIG. 6B, the balloon cover made in accordance with the present disclosure as set forth in Example 2 and overlaying the same type of nylon balloon resulted in more pronounced shoulders and thus a longer working length.

Figure 5A:
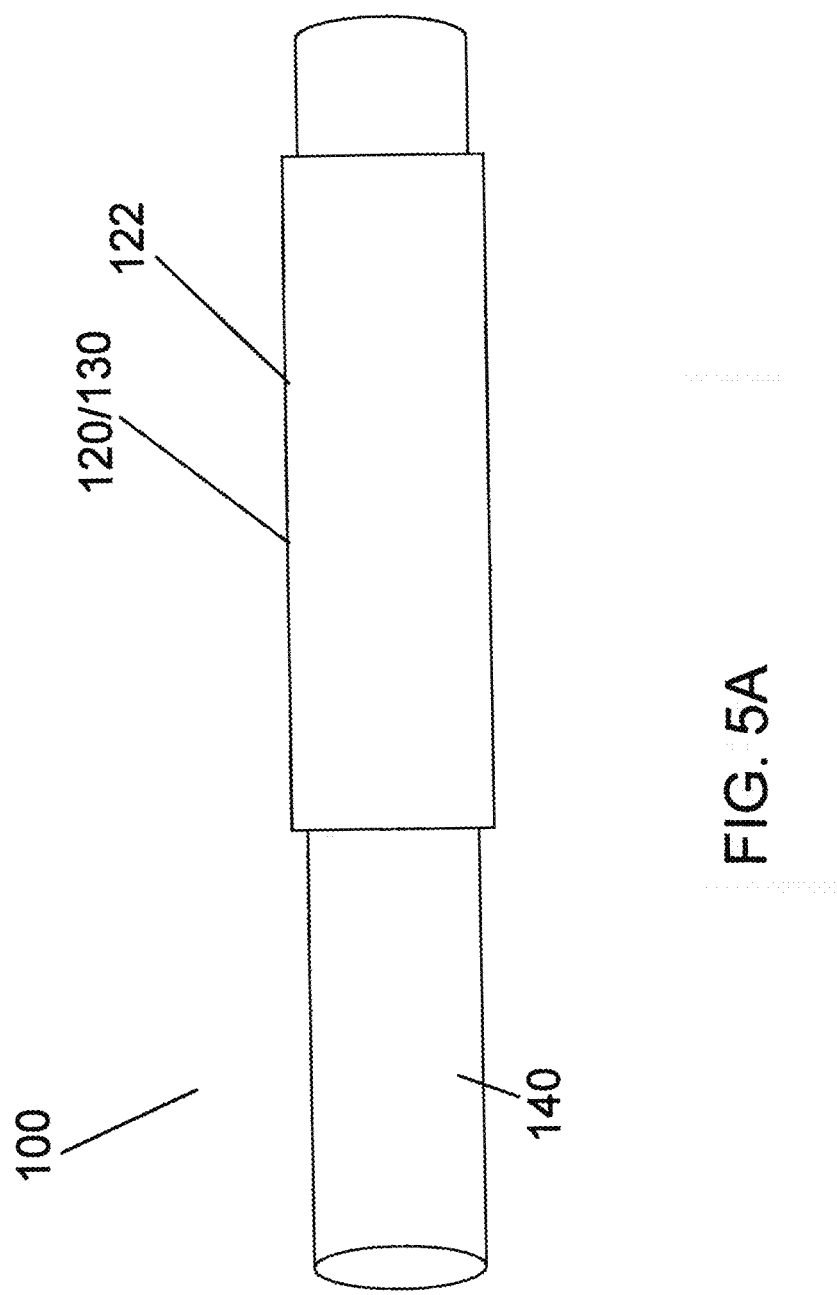
FIG. 5A is a schematic illustration of balloon device in accordance with the present disclosure in a deflated conformation.

Balloon devices of the present disclosure can be continuously wrapped into a desired shape by varying the stop points of the composite material along the length of the balloon. In various embodiments, varying the stop points can be achieved by varying the amount of tension with which the composite material is wrapped to form the balloon or balloon cover. For example, with reference to FIG. 5A and 5B, a balloon device 100 can comprise a balloon 120 or balloon cover 130 attached to a catheter 140 at or near a proximal and distal end, and have a deflated conformation and an inflated conformation. The shape of the deflated conformation can comprise a tubular form. However, in various embodiments, the shape of the inflated conformation can comprise a proximal waist 125 and a proximal tapered region 126, a distal waist 129 and distal tapered region 128, and an intermediate working region 127 between the two tapered regions 126,128. The balloon 120 or a balloon cover 130 can comprise the described composite material. The composite material can form the entire thickness of balloon 120 or a balloon cover 130 or only a portion thereof.

In order to provide a shape to a balloon, the composite material can be helically wrapped with varying degrees of tension to vary the stop point along the length of the balloon and thus yield a desired inflated shape. In addition, the composite material can be helically wrapped in a tubular form at a diameter less than the nominal diameter, e.g., approximately the delivery diameter or any diameter up to the nominal diameter. The wrap angle of the composite material can be any desired angle depending on the amount of radial distension of the material. In various embodiments, the composite material can be wrapped at substantially constant, opposing angles.

In various embodiments, the composite material can be used to construct balloons and balloon covers, as well as combinations thereof with circumferential-, helical-, or axial-orientations. As used herein, the term "axial" is interchangeable with the term "longitudinal." As used herein, "circumferential" means an angle that is substantially perpendicular to the longitudinal axis. When the composite material is applied helically versus circumferentially or axially, the degree of elasticity in a given direction can be varied. For example, if more radial distension is needed than what the stored length in the fibrils can accommodate, a helical wrap can be employed.

The composite material of the present disclosure is unique in that it exhibits a sharp increase in stiffness at a predetermined diameter, after the material has been elongated at least about 150%. When formed into a balloon, this property creates a "stop-point" beyond which increased balloon pressure does not further increase the diameter of the balloon device. Having a known stop point can help ensure that the balloon does not over-expand, which can cause, for example, over dilatation and damage a vessel. In addition, the stop point can facilitate higher working pressures of the balloon. Similarly, a balloon or balloon cover can be designed to distend at a relatively low pressure until a predetermined diameter is achieved. Upon reaching that diameter, higher pressures are required to further expand the balloon device. In other words, the slope of the diameter versus pressure curve noticeably decreases once the predetermined diameter is reached.

Figure 7A:
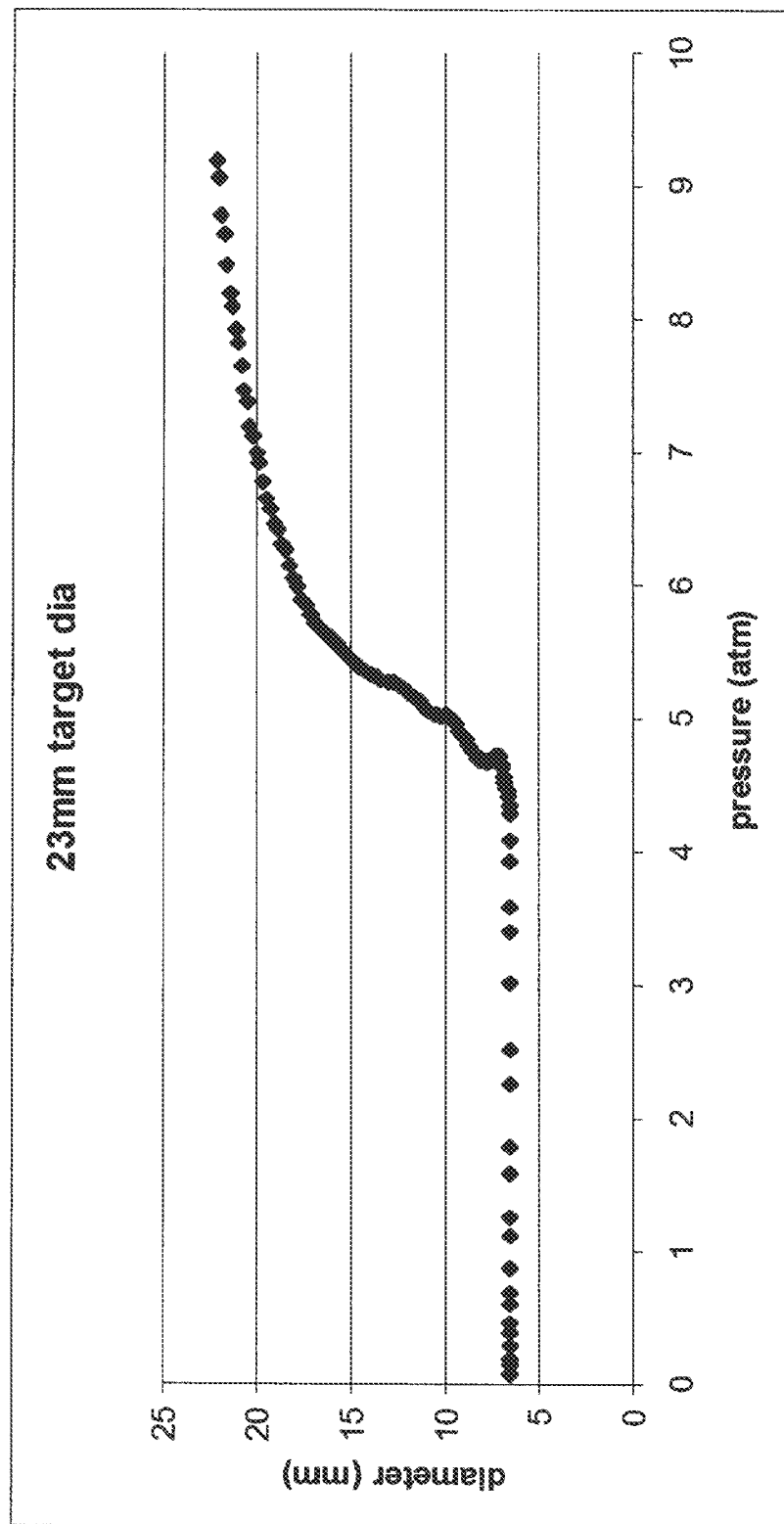
FIG. 7A is a pressure vs. diameter curve of a described balloon device.

Pressure-diameter curves relating to balloons of the present disclosure exhibit an inflection point due to the change in slope (which is directly related to the stiffness) upon reaching a diameter referred to herein as the stop point. FIG. 7A is a pressure v. diameter curve of an article according to the present disclosure, in this case a balloon, in which the intersection of two tangent lines depicts the stop point of the article. An estimate of the stop point may be determined in the following manner. The slope of the pressure-diameter curve prior to reaching the stop point can be approximated by drawing a straight line tangent to the curve, shown as line 30 in FIG. 7A. The slope of the pressure-diameter curve beyond the stop point can be approximated by drawing a straight line tangent to the curve, shown as line 40 in FIG. 7A. The diameter corresponding to the intersection of the two tangent lines, depicted by reference numeral 50, is an estimation of the stop point for the article.

Figure 7B:
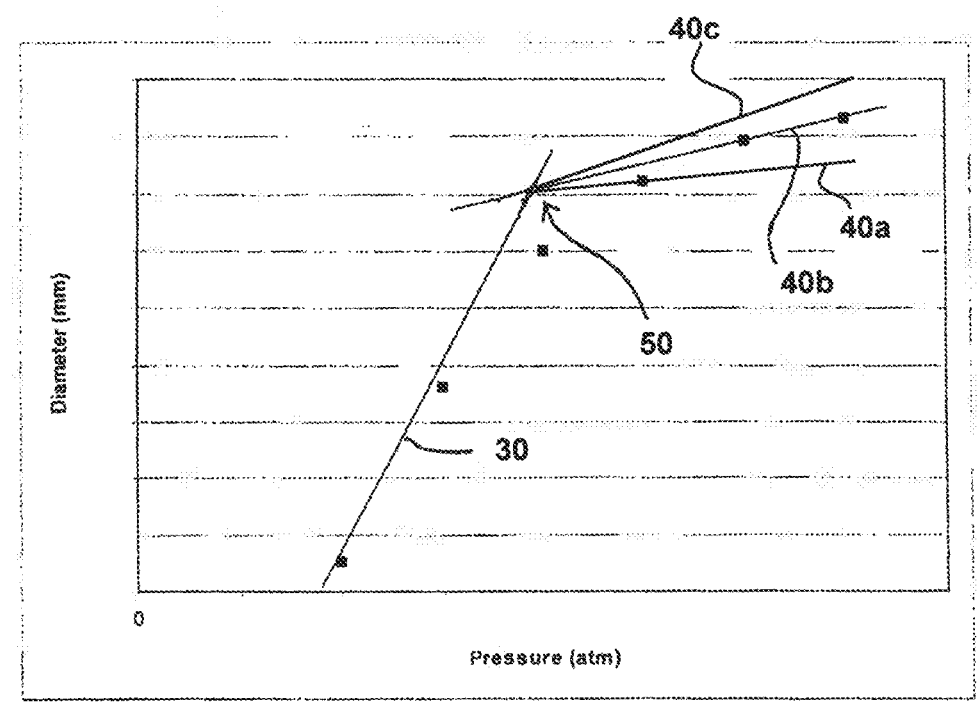
FIG. 7B is an illustrative pressure vs. diameter curve of a described balloon device.

Of course, as depicted in FIG. 7B, the stop point is not an absolute stop. The slope of line 40 can vary by varying the strength of the fluoropolymer membrane in the transverse direction versus in the machine direction, but still maintaining a relatively high amount of strength for each, or in other words, maintaining a degree of balance. If the strength of the membrane is increased in the direction that is oriented circumferentially, the slope of line 40 decreases, e.g., the slope of 40a is less than 40b, permitting less radial expansion per pressure unit. In contrast, if the strength of the membrane is decreased in the direction that is oriented circumferentially, the slope of line 40 increases, permitting more radial expansion per pressure unit. In various embodiments, membranes that are stronger in the circumferential direction (i.e., yielding a lower slope) can be weaker in the longitudinal direction. Such embodiments can facilitate a more bendable or conformable balloon that can be kink-free when inflated in a curved configuration.

Balloon devices described herein can have the ability of the balloon to be expanded in situ to dilate an occluded or partially occluded vessel and then contract approximately to the pre-inflated conformation.

In accordance with the present disclosure, a balloon or balloon cover can comprise a fluoropolymer membrane that exhibits high elongation while substantially retaining the strength properties of the fluoropolymer membrane in both the machine and transverse directions.

In accordance with the present disclosure, a balloon or balloon cover can comprise a fluoropolymer membrane that has relatively balanced strengths in the machine and traverse direction while exhibiting high elongation in at least one direction.

Such membranes characteristically possess serpentine fibrils, such as the idealized serpentine fibril exemplified in FIG. 1. As depicted generally in FIG. 1, a serpentine fibril curves or turns generally one way in the direction of arrow 10 then generally another way in the direction of arrow 20. It is to be understood that the amplitude, frequency, and periodicity of the serpentine-like fibrils as exemplified in FIG. 1 may vary. In one embodiment, the fluoropolymer membranes are expanded fluoropolymer membranes. Non-limiting examples of expandable fluoropolymers include, but are not limited to, expanded PTFE, expanded modified PTFE, and expanded copolymers of PTFE. Patents have been filed on expandable blends of PTFE, expandable modified PTFE, and expanded copolymers of PTFE, such as, for example, U.S. Pat. No. 5,708,044 to Branca; U.S. Pat. No. 6,541,589 to Baillie; U.S. Pat. No. 7,531,611 to Sabol et al.; U.S. patent application Ser. No. 11/906,877 to Ford; and U.S. patent application Ser. No. 12/410,050 to Xu et al.

The high elongation is enabled by forming relatively straight fibrils into serpentine fibrils that substantially straighten upon the application of a force in a direction opposite to the compressed direction. The creation of the serpentine fibrils can be achieved through a thermally-induced controlled retraction of the expanded polytetrafluoroethylene (ePTFE), through wetting the article with a solvent, such as, but not limited to, isopropyl alcohol or Fluorinert® (a perfluorinated solvent commercially available from 3M, Inc., St. Paul, Minn.), or by a combination of these two techniques. The retraction of the article does not result in visible pleating, folding, or wrinkling of the ePTFE, unlike what occurs during mechanical compression. The retraction also can be applied to very thin membranes, unlike known methods. During the retraction process, the fibrils not only become serpentine in shape but also may also increase in width.

The precursor materials can be biaxially expanded ePTFE membranes. In one embodiment, materials such as those made in accordance with the general teachings of U.S. Pat. No. 7,306,729 to Bacino, et al. are suitable precursor membranes, especially if small pore size articles are desired. These membranes may possess a microstructure of substantially only fibrils. The precursor membrane may or may not be amorphously locked. Additionally, the precursor membrane can be at least partially filled, coated, or otherwise combined with additional materials.

The precursor membrane may be restrained in one or more directions during the retraction process in order to prescribe the desired amount of elongation of the final article. The amount of elongation is directly related to, and is determined by, the amount of retraction.

In one embodiment, retraction can be achieved in a uniaxial tenter frame by positioning the rails at a distance less than the width of the precursor membrane prior to the application of heat or solvent or both. When using a biaxial tenter frame, one or both of the sets of grips, pins, or other suitable attachment means can similarly be positioned at a distance less than the dimensions of the precursor membrane. It is to be appreciated that these retraction means differ from the mechanical compression taught by the House and Sowinski patents noted above. Upon retraction, the expanded fluoropolymer membrane possesses serpentine fibrils. These retracted membranes characteristically possess serpentine fibrils and are substantially wrinkle free. In some exemplary embodiments, the retracted membranes may possess a microstructure of substantially only serpentine fibrils. In at least one embodiment, the fluoropolymer membranes include a plurality of serpentine fibrils. As used herein, the phrase "plurality of serpentine fibrils" is meant to denote the presence of 2 or more, 5 or more, 10 or more, or 15 or more serpentine fibrils in the fluoropolymer membrane within a field of view as taught below. The serpentine fibrils have a width of about 1.0 micron or less, and in some embodiments, about 0.5 microns or less. In one embodiment, the serpentine fibrils have a width from about 0.1 to about 1.0 microns, or from about 0.1 to about 0.5 microns.

The precursor membranes described above can be imbibed with an elastomeric material prior, during, or subsequent to retraction to form a composite material. In the absence of such elastomeric materials, fluoropolymer articles having serpentine fibrils do not exhibit appreciable recovery after elongation. Suitable elastomeric materials include, but are not limited to, PMVE-TFE (perfluoromethylvinyl ether-tetrafluoroethylene) copolymers, PAVE-TFE (perfluoro (alkyl vinyl ether)-tetrafluoroethylene) copolymers, silicones, polyurethanes, and the like. It is to be noted that PMVE-TFE and PAVE-TFE are fluoroelastomers.

In various embodiments, the described balloon or balloon covers can be used as a drug delivery balloon. By way of example, the balloon in accordance with the present disclosure can be coated with a therapeutic agent. In further embodiments, a retractable sheath (not shown) can be located about the balloon or balloon covers to prevent or minimize release of said therapeutic agent until the balloon or balloon covers is the desired treatment site.

A "therapeutic agent," as used herein, is an agent that can a bioactive response or be detectable by an analytical device. Such agents include, but are not limited to, radioopaque compounds, cilostazol, everolimus, dicumarol, zotarolimus, carvedilol, anti-thrombotic agents such as heparin, heparin derivatives, urokinase, and dextrophenylalanine proline arginine chloromethylketone; anti-inflammatory agents such as dexamethasone, prednisolone, corticosterone, budesonide, estrogen, sulfasalazine and mesalamine, sirolimus and everolimus (and related analogs), anti-neoplastic/anti-proliferative/anti-miotic agents such as major taxane domain-binding drugs, such as paclitaxel and analogues thereof, epothilone, discodermolide, docetaxel, paclitaxel protein-bound particles such as ABRAXANE® (ABRAXANE is a registered trademark of ABRAXIS BIOSCIENCE, LLC), paclitaxel complexed with an appropriate cyclodextrin (or cyclodextrin like molecule), rapamycin and analogues thereof, rapamycin (or rapamycin analogs) complexed with an appropriate cyclodextrin (or cyclodextrin like molecule), 17β-estradiol, 17β-estradiol complexed with an appropriate cyclodextrin, dicumarol, dicumarol complexed with an appropriate cyclodextrin, β-lapachone and analogues thereof, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, AZX100 a cell peptide that mimics HSP20 (Capstone Therapeutics Corp., USA), heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; agents that interfere with endogenous vasoactive mechanisms; inhibitors of leukocyte recruitment, such as monoclonal antibodies; cytokines; hormones or a combination thereof. In one embodiment, said therapeutic agent is a hydrophilic agent. In another embodiment, said therapeutic agent is a hydrophobic agent. In another embodiment, said therapeutic agent is paclitaxel.

In accordance with the present disclosure, as previously described, the described balloon cover or balloon, because of its elastic properties, can be constructed at a delivery diameter or at any other diameter less than the nominal diameter. The ability of the cover of the balloon or balloon cover to be constructed at a smaller diameter means ease of manufacturing as well as less material used to construct the balloon or the balloon cover leading to less bulk or, i.e., a lower delivery and/or retraction profile.

Most balloons are formed at a larger second or nominal diameter and pleated/folded down to a delivery profile. Pleating and folding a drug coated balloon can cause the coating to come off or particulate and/or can require a high level of adhesion of the coating to the balloon to mitigate particulation. The described balloon devices can be created at a smaller diameter and require less or no pleating in the delivery conformation. No or reduced folding can allow for a more even coating to be applied and/or allow for less disruption to the coating upon inflation. Furthermore, the composite material will be strained 200-500% during inflation which can aid in drug transfer to the vessel.

Having generally described this disclosure, a further understanding can be obtained by reference to certain specific examples illustrated below which are provided for purposes of illustration only and are not intended to be all inclusive or limiting unless otherwise specified.

Testing Methods

It should be understood that although certain methods and equipment are described below, any method or equipment determined suitable by one of ordinary skill in the art may be alternatively utilized.

Mass, Thickness, and Density

Membrane samples can be die cut to form rectangular sections about 2.54 cm by about 15.24 cm to measure the weight (using a Mettler-Toledo analytical balance model AG204) and thickness (using a Kafer Fz1000/30 snap gauge). Using these data, density can be calculated with the following formula: $\rho=m/(w*l*t)$, in which: $\rho$=density (g/cm$^3$), m=mass (g), w=width (cm), l=length (cm), and t=thickness (cm). The average of three measurements will be reported.

Matrix Tensile Strength (MTS) of Membranes

Tensile break load can be measured using an INSTRON 122 tensile test machine equipped with flat-faced grips and a 0.445 kN load cell. The gauge length can be about 5.08 cm and the cross-head speed can be about 50.8 cm/min. The sample dimensions can be about 2.54 cm by about 15.24 cm. For highest strength measurements, the longer dimension of the sample can be oriented in the highest strength direction. For the orthogonal MTS measurements, the larger dimension of the sample can be oriented perpendicular to the highest strength direction. Each sample can be weighed using a Mettler Toledo Scale Model AG204, then the thickness can be measured using the Kafer FZ1000/30 snap gauge; alternatively, any suitable means for measuring thickness may be used. The samples can then be tested individually on the tensile tester. Three different sections of each sample can be measured. The average of the three maximum loads (i.e., peak force) measurements can be reported. The longitudinal and transverse matrix tensile strengths (MTS) can be calculated using the following equation: MTS=(maximum load/cross-section area)*(bulk density of PTFE)/(density of the porous membrane), where an example of the bulk density of the PTFE can be about 2.2 g/cm$^3$.

Pressure vs. Diameter Test

A pressure versus diameter curve can be created by radially expanding a balloon and a described balloon cover using an inflation syringe to pressurize a balloon catheter. The diameter of the construct can be measured at desired intervals, e.g., 0.1 ATM to 1 ATM intervals, using a laser micrometer.

EXAMPLES

Example 1

An elastomeric composite material was made in the following manner.

Precursor Membrane

A biaxially expanded ePTFE membrane that had not been amorphously locked and had the following properties was obtained: thickness was approximately 0.001 mm, density was approximately 0.964 g/cc, matrix tensile strength in the strongest direction was approximately 451 MPa, matrix tensile strength in the direction orthogonal to the strongest direction was approximately 320 MPa, elongation at maximum load in the strongest direction was approximately 92%, and elongation at maximum load in the direction orthogonal to the strongest direction was approximately 142%. Upon tensioning by hand, the membrane did not noticeably retract upon the release of the tension.

Retracted Membrane

A roll of precursor membrane where the length direction corresponded with the weakest direction of the membrane was restrained in the clamps of a heated, uniaxial tenter frame and fed into the heated chamber of the tenter frame. The oven temperature was set to about 300° C. The rails of the tenter frame within the heated chamber were angled inward in order to allow membrane shrinkage to about 20% of its original width in response to the heat. The line speed was set to provide a dwell time of about 2.1 minutes within the heated chamber.

The initial and final widths of the membrane were 1537 mm and 305 mm, respectively. The retracted membrane had the following properties: thickness was approximately 0.0018 mm, density was approximately 2.3 g/cc, matrix tensile strength in the strongest direction of the precursor membrane was approximately 454 MPa, matrix tensile strength in the direction orthogonal to the strongest direction of the precursor membrane was approximately 61 MPa, elongation at maximum load in strongest direction of the precursor membrane was approximately 142%, and elongation at maximum load in the direction orthogonal to the strongest direction of the precursor membrane was approximately 993%.

Elastomeric Composite Material

A polyurethane elastomer (Tecothane® TT-1074A) was dissolved in tetrahydrofuran to a concentration of about 6.5% wt. The solution was coated using a slot die coating process operating at a line speed of approximately 1.8 m/min and a solution coating rate of approximately 96 g/min was utilized to imbibe this solution into an ePTFE membrane that was fed from a roll. The percent weight of the elastomer within the composite material was about 75%.

Figure 2:
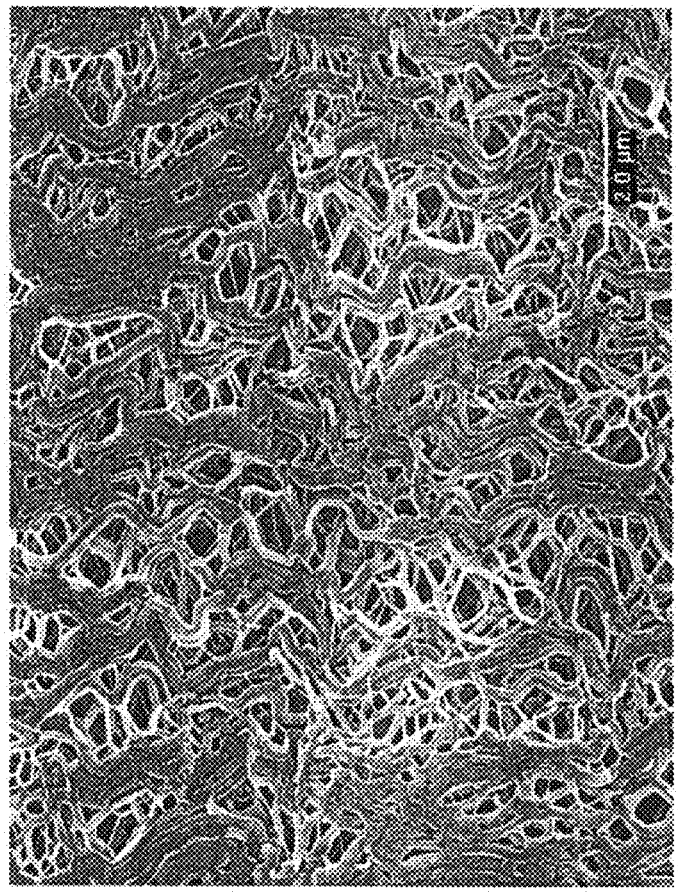
FIG. 2 is an SEM image of a composite material comprising serpentine fibrils.

The elastomeric composite material had the following properties: thickness was approximately 0.014 mm (calculated) and width was approximately 229 mm. In order to better visualize the serpentine fibrils, a length of the same elastomeric composite material was stretched by hand to about 78% of the original length. As stretched, the fibrils were seen to have a serpentine shape as indicated in FIG. 2, an SEM image of the surface of the membrane opposing the imbibed elastomer (i.e., the ePTFE rich side), taken at 5,000× magnification.

The tensile strength of this elastomeric composite was about 104 MPa.

Example 2

A balloon cover was constructed in the following manner. An ePTFE-fluoropolymer elastomeric composite material as described in detail above was obtained. A mandrel sized to delivery diameter, approximately 4.3 mm is obtained. It was noted that the length direction of the composite material was the direction that possessed the elastomeric properties.

The composite material was cut to 100 mm width, measuring in the machine direction. The composite material was cut to 250 mm length, measuring in the transverse direction. The 250 mm length was then cut into two, 125 mm lengths, measuring in the transverse direction.

The composite material was aligned so that the 4.3 mm mandrel was parallel with the machine direction of the material. The film was then circumferentially wrapped about the mandrel with the side of the membrane opposing the imbibed elastomer oriented toward the mandrel. The second 125 mm length was then circumferentially wrapped about the mandrel with the side of the membrane opposing the imbibed elastomer oriented away from the mandrel. No or minimal tension was applied to the composite material during wrapping.

Three layers of sacrificial ePTFE film were wrapped around the composite material and the mandrel was placed in the oven for 3 minutes at 235 degrees Celsius. Once removed from the oven, the sacrificial wrap was removed and discarded. The tubular form of composite material is then trimmed to 85 mm in tubular length.

The balloon cover was slid over a pleated and folded 23 mm diameter nylon balloon supplied by Vention Medical and secured to the catheter at the proximal and distal ends of the balloon.

Example 3

A balloon cover was constructed in the following manner. An ePTFE-fluoropolymer elastomeric composite material was obtained. This composite utilized an expanded ePTFE membrane—made generally in accordance with U.S. Pat. No. 5,476,589 to Bacino which is hereby incorporated by reference in its entirety—had the following properties: thickness was approximately 6.3 µm, mass per area was approximately 3 g/m$^2$, matrix tensile strength in the strongest direction was approximately 917 mPa, matrix tensile strength in the direction orthogonal to the strongest direction was approximately 17.2 mPa. The membrane was coated similarly to the composite of Example 1. A mandrel sized to delivery diameter, approximately 4.3 mm is obtained.

The composite material was cut to 100 mm width, measuring in the machine direction. It is noted that this width direction is the strongest direction. The composite material was cut to 250 mm length, measuring in the transverse direction. The 250 mm length was then cut into two, 125 mm lengths, measuring in the transverse direction.

The composite material was aligned so that the 4.3 mm mandrel was parallel with the machine direction of the material. The film was then circumferentially wrapped about the mandrel with the side of the membrane opposing the imbibed elastomer oriented toward the mandrel. The second 125 mm length was then circumferentially wrapped about the mandrel with the side of the membrane opposing the imbibed elastomer oriented away from the mandrel. No or minimal tension was applied to the composite material during wrapping.

Three layers of sacrificial ePTFE film were wrapped around the composite material and the mandrel was placed in the oven for 3 minutes at 235 degrees Celsius. Once removed from the oven, the sacrificial wrap was removed and discarded. The tubular form of composite material is then trimmed to 85 mm in tubular length.

The balloon cover was slid over a pleated and folded 23 mm diameter nylon balloon supplied by Vention Medical and secured to the catheter at the proximal and distal ends of the balloon.

Example 4

A balloon cover was constructed in the following manner. An ePTFE-fluoropolymer elastomeric composite material as described in detail above was obtained. A mandrel sized to delivery diameter, approximately 4.3 mm was obtained. It was noted that the length direction of the composite material was the direction that possessed the elastomeric properties.

Figure 8A:
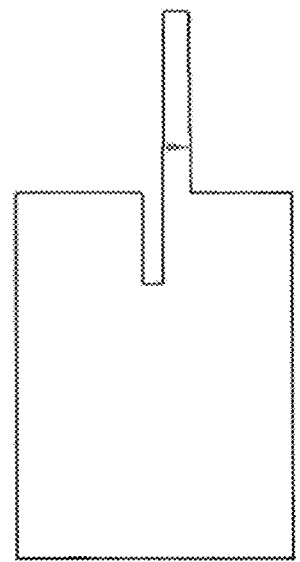
FIG. 8A is a schematic illustration of a template for a precursor for a balloon or balloon cover having varied stiffness along the length in accordance with the present disclosure.

The composite material was cut to 150 mm width, measured in the machine direction. Using the template shown in FIG. 8A, base of template was aligned with machine direction and cut film to specified geometry. (Other template shapes can be used to vary the number of layers along the length of the tubular form. The template shape can comprise at least a first portion having a first length and a second portion having a second length. Said templates can have staggered edge(s) or curved edge(s) resulting in a distinct to a more gradual variation in the number of layers along the length of the tubular form.)

The composite material was aligned so that the 4.3 mm mandrel was parallel with the longitudinal direction of the material. The film was then circumferentially wrapped about the mandrel with the ePTFE rich side toward the mandrel. No or minimal tension was applied to the composite material during wrapping.

Figure 8B:
FIG. 8B is a schematic illustration of a wrapped balloon or balloon cover having varied stiffness along the length in accordance with the present disclosure.

Three layers of sacrificial ePTFE film were wrapped around the composite material and the mandrel was placed in the oven set to 235 degrees Celsius for 3 minutes. Once removed from the oven, the sacrificial wrap was removed and discarded. The tubular form of composite material was then trimmed to 85 mm, as shown in FIG. 8B.

The balloon cover was slid over a pleated and folded 23 mm diameter nylon balloon supplied by Vention Medical and secured to the catheter at the proximal and distal ends of the balloon.

What is claimed is:

1. A medical balloon cover having a longitudinal axis comprising:
a balloon cover comprising at least one expanded fluoropolymer material,
wherein said expanded fluoropolymer material comprises a plurality of serpentine fibrils,
wherein the balloon cover is wrapped at a delivery diameter, the balloon cover being substantially wrinkle free at the delivery diameter, and
wherein the balloon cover has a nominal diameter that is at least 3 times greater than the delivery diameter of the balloon cover upon expansion by a balloon.

2. The medical balloon cover of claim 1, wherein the expanded fluoropolymer material comprises polytetrafluoroethylene.

3. The medical balloon cover of claim 1, wherein the expanded fluoropolymer material comprises a microstructure of substantially only fibrils.

4. The medical balloon cover of claim 1, wherein said balloon cover is more resistant to expanding to a second expanded diameter from the nominal diameter upon further expansion of the balloon than from the delivery diameter to the nominal diameter, and wherein the second expanded diameter is greater than the nominal diameter.

5. The medical balloon cover of claim 1, wherein said expanded fluoropolymer material is axially wrapped.

6. The medical balloon cover of claim 1, wherein said expanded fluoropolymer material is helically wrapped.

7. The medical balloon cover of claim 1, wherein said expanded fluoropolymer material is wrapped in at least two of the following orientations: helically, axially, and circumferentially.

8. The medical balloon cover of claim 1, wherein each said serpentine fibril has a width of about 1.0 micron or less.

9. The medical balloon cover of claim 8, wherein each said serpentine fibril has a width of 0.5 micron or less.

10. The medical balloon cover of claim 1, wherein said expanded fluoropolymer material is imbibed with an elastomer.

11. The medical balloon cover of claim 10, wherein the balloon cover further comprises an elastomer that is selected from the group consisting of perfluoromethylvinyl ether-tetrafluoroethylene copolymers, perfluoro(alkyl vinyl ether)-tetrafluoroethylene copolymers, silicones, polyurethanes, or other high strain elastomers.

12. The medical balloon cover of claim 11, wherein elastic properties are present in a direction parallel to the longitudinal axis of the medical balloon.

13. The medical balloon cover of claim 11, wherein elastic properties are present in a radial direction of the medical balloon.

14. The medical balloon cover of claim 11, wherein said elastomer is present in pores of said expanded fluoropolymer material.

15. The medical balloon cover of claim 11, wherein said at least one expanded fluoropolymer material comprises a plurality of pores and said elastomer is present in substantially all of said pores.

16. The medical balloon cover of claim 1, wherein said expanded fluoropolymer material is circumferentially wrapped to form a tubular form.

17. The medical balloon cover of claim 16, wherein said expanded fluoropolymer material comprises a plurality of layers, wherein a first section of the tubular form has a higher number of layers than a second section of the tubular form.

18. The medical balloon cover of claim 17, wherein said expanded fluoropolymer material is continuously wrapped into a tubular form.

19. A medical balloon cover having a longitudinal axis comprising a balloon cover comprising at least one expanded fluoropolymer material, wherein said expanded fluoropolymer material comprises a plurality of serpentine fibrils, wherein said balloon cover is circumferentially wrapped at a delivery diameter in which the serpentine fibrils are arranged in a circumferential direction, wherein said balloon cover can be radially expanded up to a nominal diameter beyond which further expansion is inhibited by expansion of a balloon, and wherein said nominal diameter is at least 3 times greater than the delivery diameter;

wherein the balloon cover is circumferentially wrapped at the delivery diameter such that the balloon cover is substantially wrinkle free at the delivery diameter.

20. The medical balloon cover of claim 19, wherein said nominal diameter is at least 4 times greater than the delivery diameter.

21. The medical balloon cover of claim 19, wherein said nominal diameter is at least 6 times greater than the delivery diameter.

22. The medical balloon cover of claim 19, wherein said nominal diameter at least 8 times greater than the delivery diameter.

23. The medical balloon cover of claim 19, wherein said nominal diameter is at least 10 times greater than the delivery, diameter.

24. The medical balloon cover of claim 19, wherein the expanded fluoropolymer material comprises polytetrafluoroethylene.

25. The medical balloon cover of claim 19, wherein the expanded fluoropolymer material comprises a microstructure of substantially only fibrils.

26. The medical balloon cover of claim 19, wherein the expanded fluoropolymer material comprises a microstructure of substantially only serpentine fibrils.

27. The medical balloon cover of claim 19 wherein said balloon cover comprises a plurality of layers, wherein a first section of balloon cover has a higher number of layers than a second section of the balloon cover.

28. The medical balloon cover of claim 19, wherein each said serpentine fibril has a width of about 1.0 micron or less.

29. The medical balloon cover of claim 28, wherein each said serpentine fibril has a width of 0.5 micron or less.

30. The medical balloon cover of claim 19, wherein the balloon cover further comprises an elastomer that is selected from the group consisting of perfluoromethylvinyl ether-tetrafluoroethylene copolymers, perfluoro(alkyl vinyl ether)-tetrafluoroethylene copolymers, silicones, polyurethanes, or other high strain elastomers.

31. The medical balloon cover of claim 30, wherein elastic properties are present in a direction parallel to the longitudinal axis of the medical balloon cover.

32. The medical balloon cover of claim 30, wherein elastic properties are present in a radial direction of the medical balloon.

33. The medical balloon cover of claim 30, wherein said at least one expanded fluoropolymer material comprises a plurality of pores and said elastomer is present in at least of portion of said pores.

34. The medical balloon cover of claim 30, wherein said at least one expanded fluoropolymer material comprises a plurality of pores and the elastomer that is selected from the group consisting of perfluoromethlyinyl ether-tertrafluoroethylene copolymers, perfluoro(alkyl vinyl ether)-tetrafluoroethylene copolymers, silicones, polyurethanes, or other high strain elastomers is present in substantially all of said pores.

* * * * *